US011154540B2

(12) United States Patent
Matsuda

(10) Patent No.: US 11,154,540 B2
(45) Date of Patent: Oct. 26, 2021

(54) METHODS OF TREATING OPHTHALMIC DISEASE/DISORDER OR INJURY WITH IBUDILAST

(71) Applicant: MediciNova, Inc., La Jolla, CA (US)

(72) Inventor: Kazuko Matsuda, La Jolla, CA (US)

(73) Assignee: MediciNova, Inc., La Jolla, CA (US)

( * ) Notice: Subject to any disclaimer, the term of this patent is extended or adjusted under 35 U.S.C. 154(b) by 0 days.

(21) Appl. No.: 16/657,276

(22) Filed: Oct. 18, 2019

(65) Prior Publication Data

US 2020/0121659 A1 Apr. 23, 2020

Related U.S. Application Data

(60) Provisional application No. 62/748,148, filed on Oct. 19, 2018.

(51) Int. Cl.
| | | |
|---|---|---|
| *A61K 31/395* | (2006.01) | |
| *A61K 31/4355* | (2006.01) | |
| *A61P 25/28* | (2006.01) | |
| *A61K 9/00* | (2006.01) | |

(52) U.S. Cl.
CPC .......... *A61K 31/4355* (2013.01); *A61P 25/28* (2018.01); *A61K 9/0053* (2013.01)

(58) Field of Classification Search
CPC .................................................. A61K 31/395
See application file for complete search history.

(56) References Cited

U.S. PATENT DOCUMENTS

| 6,395,747 | B1 | 5/2002 | Sakoda et al. |
| 8,138,201 | B2 | 3/2012 | Kalafer et al. |
| 9,314,452 | B2 | 4/2016 | Kalafer et al. |
| 2006/0160843 | A1 | 7/2006 | Johnson et al. |
| 2017/0360762 | A1 | 12/2017 | Matsuda et al. |

FOREIGN PATENT DOCUMENTS

WO  WO-2009009529 A1 * 1/2009 ............. A61K 45/06

OTHER PUBLICATIONS

Green, Ari J., et al. "Ocular pathology in multiple sclerosis: retinal atrophy and inflammation irrespective of disease duration." Brain. (2010), vol. 133, pp. 1591-1601. (Year: 2010).*
Belforte et al., "The phosphodiesterase Inhibitor Ibudilast Attenuates Glial Cell Reactivity, Production of Proinflammatory Cytokines and Neural Loss in Experimental Glaucoma", ARVO Annual Meeting Abstract, Apr. 2014, two (2) pages.
Bermel et al., "Effect of Ibudilast on Macular Measures in Progressive MS: OCT Analysis from a Phase II Trial", Neurology: Official Journal of the American Academy of Neurology; 71st Annual Meeting. American Academy of Neurology, vol. 92, No. 15, Supplement 1, Apr. 1, 2019, pp. P3. 2-049.
Bremel et al., "Effect of Ibudilast on Macular Measures in Progressive MS; OCT Analysis From the SPRINT-MS Trial", 71st Annual Meeting. American Academy of Neurology; May 4-10, 2019; Philadelphia, US, May 7, 2019, p. 1.
International Search Report and Written Opinion issued in International Application No. PCT/US2019/056948 dated Feb. 10, 2020.
Lavinsky et al., "Chronic Bilateral Common Carotid Artery Occlusion: a Model for Ocular Ischemic Syndrome in the Rat", Graefe's Archive for Clinical and Experimental Ophthalmogy, vol. 244, No. 2, Feb. 1, 2006, pp. 199-204.
Margeta et al., "CD163 Macrophages Infiltrate Axon Bundles of Postmortem Optic Nerves with Glaucoma", Graefe's Archive for Clinical and Experimental Ophthamology, vol. 256, No. 12, Aug. 2, 2018, pp. 2449-2456.
Tominga et al., "Protective Effects of Ibudilast on Glutamate Neurotoxicity in Cultured Hoppocampal Neurons", neuroscience Research Supplement, vol. 19, Jan. 1, 1994, p. S63.
Vargas et al., "The Glial Cell Modulator Ibudilast Attenuates Neuroinflammation and Enhances Retinal Ganglion Cell Viability in Glaucoma Through Protein Kinase A Signaling", Neurobiology of Disease, vol. 93, May 6, 2016, pp. 156-171.
Gibson et al., "The Inhibitory Profile of Ibudilast Against the Human Phosphodiesterase Enzyme Family," European Journal of Pharmacology, vol. 538, pp. 39-42 (2006).
Sanftner et al., "Cross-species comparisons of the pharmacokinetics of ibudilast," Xenobiotica, vol. 39, No. 12, pp. 964-977 (Nov. 2009). [Abstract].
Mizuno et al., "Neuroprotective role of phosphodiesterase inhibitor ibudilast on neuronal cell death induced by activated microglia," Neuropharmacology, vol. 46, pp. 404-411(2004).
Obernolte, R., et al. "The cDNA of a human lymphocyte cyclic-AMP phosphodiesterase (PDE IV) reveals a multigene family" Gene 129: 239-247 (1993).
Rile et al., "Potentiation of Ibudilast Inhibition of Platelet Aggregation in the Presence of Endothelial Cells," Thrombosis Research, 102 239-246 (2001).
Souness et al., "Possible Role of Cyclic AMP Phosphodiesterases in the Actions of Ibudilast on Eosinophil Thromboxane Generation and Airways Smooth Muscle Tone," British Journal of Pharmacology, 111:1081-1088 (1994).
Suzumura et al., "Ibudilast suppresses TNF.alpha. production by glial cells functioning mainly as type III phosphodiesterase inhibitor in NCS," Brain Research, 837:203-212 (1999).
Takuma et al., "Ibudilast attenuates actrocyte apoptsis via cyclic GMP signaling pathway in an in vitro reperfusion model," British Journal of Pharmacology, 133:841-848 (2001).
Jeffery et al., "The Preparation and Characterization of Poly(lactide-co-glycolide) Microparticles. II. The Entrapment of a Model Protein Using a (Water-in-Oil)-in-Water Emulsion Solvent Evaporation Technique", Pharmaceutical Research, vol. 10, No. 3, pp. 362-368 (1993).

(Continued)

*Primary Examiner* — John S Kenyon
(74) *Attorney, Agent, or Firm* — Foley & Lardner LLP

(57) ABSTRACT

This disclosure is directed to methods of treating ophthalmic disease/disorder or injury associated with neurodegenerative disease/disorder, such as progressive multiple sclerosis, or a neuro-ophthalmologic disorder in human patients using ibudilast.

20 Claims, 1 Drawing Sheet

(56) References Cited

OTHER PUBLICATIONS

Cho et al., "Allosteric Inhibition of Macrophage Migration Inhibitory Factor revealed by Ibudilast," *PNAS* vol. 107, No. 25, pp. 11313-11318 (Jun. 2010).

Yang, et al., "The Emerging Role of Toll-Like Receptor 4 in Myocardial Inflammation," *Cell Death and Disease*, vol. 7, 10 pages (May 2016).

Fox, et al., "Phase 2 Trial of Ibudilast in Progressive Multiple Sclerosis," *The New England Journ. of Medicine*, pp. 846-855 (2018).

* cited by examiner

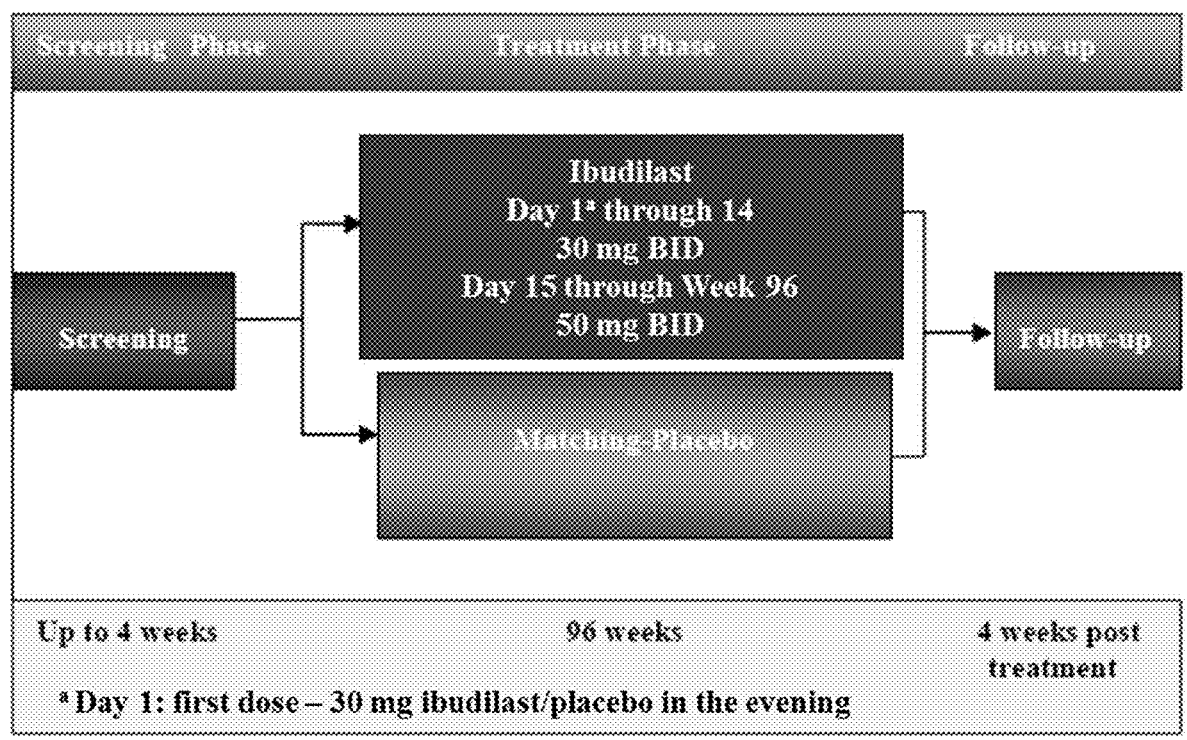

METHODS OF TREATING OPHTHALMIC DISEASE/DISORDER OR INJURY WITH IBUDILAST

CROSS-REFERENCE TO RELATED APPLICATIONS

This application claims the benefit of priority of U.S. Provisional Patent Application No. 62/748,148, filed Oct. 19, 2018, which is incorporated by reference herein in its entirety.

STATEMENT OF GOVERNMENT SUPPORT

This invention was created in the performance of a Cooperative Research and Development Agreement with the National Institutes of Health, an Agency of the Department of Health and Human Services. The Government of the United States has certain rights in this invention.

BACKGROUND

The small molecule ibudilast (3-isobutyryl-2-isopropylpyrazolo[1,5-a]pyridine) is an inhibitor of macrophage inhibitory factor (MIF) (Cho et al., PNAS-USA, 2010 June 107: 11313-8), is a selective inhibitor of cyclic nucleotide phosphodiesterases (PDEs) 3A, 4, 10A1 and 11A1 (Gibson et al., Eur. J. Pharmacol., 538: 39-42, 2006), and has toll-like receptor-4 (TLR4) antagonistic activity (Yang et al., Cell Death and Disease (2016) 7, e2234; doi:10.1038/cddis.2016.140). Ibudilast distributes well to the CNS (Sanftner et al., Xenobiotica, 2009 39: 964-977) and at clinically-relevant plasma or CNS concentrations, ibudilast selectively inhibits macrophage migration inhibitory factor (MIF) and, secondarily, PDEs 3, 4, 10 and 11. Ibudilast also acts as a leukotriene D4 antagonist, an anti-inflammatory, a PAF antagonist, and a vasodilatory agent (Thompson Current Drug Reports). Ibudilast is thought to exert a neuroprotective role in the central nervous system of mammals, presumably via suppression of the activation of glial cells (Mizuno et al., Neuropharmacology 46: 404-411, 2004).

Ibudilast has been widely used in Japan for relieving symptoms associated with ischemic stroke or bronchial asthma. In recent clinical trials, its use in the treatment of multiple sclerosis (MS), an inflammatory disease of the central nervous system, has been explored (News.Medical.Net; Pharmaceutical News, 2 Aug. 2005). As disclosed in this publication, this clinical trial was expected to treat "relapsing-remitting MS," however, no mention is made of progressive multiple sclerosis. In U.S. Pat. No. 6,395,747, ibudilast is disclosed as a treatment for multiple sclerosis, which is generally understood to mean relapsing and remitting multiple sclerosis, not progressive multiple sclerosis. U.S. Patent Application Publication No. 20060160843 discloses ibudilast for the treatment of intermittent and short-term pain, however, this is not pain related to a progressive neurodegenerative disease. However, U.S. Pat. No. 9,314,452 discloses ibudilast as a treatment for amyotrophic lateral sclerosis, a progressive neurodegenerative disease. Similarly, U.S. Pat. No. 8,138,201 discloses ibudilast as a treatment for primary progressive multiple sclerosis and/or secondary progressive multiple sclerosis.

The use of ibudilast for treating macular injury associated with progressive multiple sclerosis has heretofore remained largely unexplored.

SUMMARY

In one aspect, provided herein is a method of treating ophthalmic disease/disorder or injury associated with a neurodegenerative disease/disorder or a neuro-ophthalmologic disorder in a human patient in need thereof comprising administering to the human patient a therapeutically effective amount of ibudilast, or a pharmaceutically acceptable salt thereof. In some embodiments, the ophthalmic disease/disorder or injury is macular injury. In some embodiments, the neurodegenerative disease/disorder is progressive multiple sclerosis.

In another aspect, provided herein is a method of decreasing macular volume loss associated with a progressive multiple sclerosis in a human patient in need thereof comprising administering to the human patient a therapeutically effective amount of ibudilast, or a pharmaceutically acceptable salt thereof. In some embodiments, the administration of the ibudilast, or pharmaceutically acceptable salt thereof, decreases macular volume loss in the human patient as compared to no administration of the ibudilast, or pharmaceutically acceptable salt thereof.

In some embodiments, the progressive multiple sclerosis has progressed beyond relapse remitting multiple sclerosis. In some embodiments, the progressive multiple sclerosis is primary progressive multiple sclerosis. In some embodiments, the primary progressive multiple sclerosis is characterized by disease progression from onset, with occasional plateaus and temporary minor improvements allowed, but not distinct relapses.

In some embodiments, the progressive multiple sclerosis is secondary progressive multiple sclerosis. In some embodiments, the secondary progressive multiple sclerosis is characterized as an initial relapsing-remitting course, followed by progression, with or without occasional relapses, minor remissions and plateaus.

In some embodiments, the ibudilast, or pharmaceutically acceptable salt thereof, is administered for at least about 12, 24, 36, 48, 60, 72, 84, or 96 weeks. In some embodiments, the ibudilast, or pharmaceutically acceptable salt thereof, is administered for about 12, 24, 36, 48, 60, 72, 84, or 96 weeks. In some embodiments, the ibudilast, or pharmaceutically acceptable salt thereof, is administered for at least about 1 year, 2 years, 3 years, 4 years, or 5 years. In some embodiments, the ibudilast, or pharmaceutically acceptable salt thereof, is administered for 1 year, 2 years, 3 years, 4 years, or 5 years.

In some embodiments, the ibudilast, or pharmaceutically acceptable salt thereof, is administered orally. In some embodiments, the ibudilast, or pharmaceutically acceptable salt thereof, is administered in a tablet, capsule, granule, or microbead dosage form. In some embodiments, the ibudilast, or pharmaceutically acceptable salt thereof, is administered in in a liquid dosage form. In some embodiments, the ibudilast, or pharmaceutically acceptable salt thereof, is formulated as an extended release formulation.

In some embodiments, ibudilast, or pharmaceutically acceptable salt thereof, is administered in an amount of from about 0.1 mg/day to about 4,000 mg/day. In some embodiments, ibudilast, or pharmaceutically acceptable salt thereof, is administered in an amount of from about 0.1 mg/day to about 720 mg/day. In some embodiments, ibudilast, or pharmaceutically acceptable salt thereof, is administered in an amount of at least about 30 mg/day. In some embodiments, the ibudilast, or pharmaceutically acceptable salt thereof, is administered in an amount of from about 30 mg/day to about 200 mg/day. In some embodiments, the ibudilast, or pharmaceutically acceptable salt thereof, is administered in an amount of from about 60 mg/day to about 600 mg/day. In some embodiments, the ibudilast, or pharmaceutically acceptable salt thereof, is administered in an amount of from about 60 mg/day to about 100 mg/day. In some embodiments, the ibudilast, or pharmaceutically acceptable salt thereof, is administered in an amount of from about 100 mg/day to about 480 mg/day.

In some embodiments, the ibudilast, or pharmaceutically acceptable salt thereof, is administered in an amount of about 30 mg/day, about 60 mg/day, about 80 mg/day, about 90 mg/day, about 100 mg/day, about 120 mg/day, about 150 mg/day, about 180 mg/day, about 210 mg/day, about 240 mg/day, about 270 mg/day, about 300 mg/day, about 360 mg/day, about 400 mg/day, about 440 mg/day, about 480 mg/day, about 520 mg/day, about 580 mg/day, about 600 mg/day, about 620 mg/day, about 640 mg/day, about 680 mg/day, or about 720 mg/day. In some embodiments, the ibudilast, or pharmaceutically acceptable salt thereof, is administered in an amount of about 60 mg/day, about 80 mg/day, or about 100 mg/day. In some embodiments, the amount of ibudilast, or pharmaceutically acceptable salt thereof, administered per day is divided into one, two or three portions.

BRIEF DESCRIPTION OF THE FIGURES

The FIGURE illustrates the study design.

DETAILED DESCRIPTION

This disclosure relates to the treatment or alleviation of ophthalmic disease/disorder or injury associated with neurodegenerative disease/disorder, such as but not limited to progressive forms of multiple sclerosis, or neuro-ophthalmologic disorder. In some embodiments, the progressive form of multiple sclerosis is exclusive of relapse/remitting multiple sclerosis. The disclosed technology is directed to use of ibudilast, or a pharmaceutically acceptable salt thereof, for human patients with ophthalmic disease/disorder or injury associated with neurodegenerative disease/disorder or neuro-ophthalmologic disorder.

In some embodiments, provided herein are methods of treating ophthalmic disease/disorder or injury associated with a neurodegenerative disease/disorder or a neuro-ophthalmologic disorder in a human patient in need thereof comprising, consisting essentially of, or consisting of administering to the human patient a therapeutically effective amount of ibudilast, or a pharmaceutically acceptable salt thereof. In some embodiments, the ophthalmic disease/disorder or injury is macular injury. In some embodiments, the neurodegenerative disease/disorder is progressive multiple sclerosis.

In some embodiments, provided herein are methods of treating ophthalmic disease/disorder or injury associated with a neurodegenerative disease/disorder in a human patient in need thereof comprising, consisting essentially of, or consisting of administering to the human patient a therapeutically effective amount of ibudilast, or a pharmaceutically acceptable salt thereof.

In some embodiments, provided herein are methods of treating retinal injury associated with a neurodegenerative disease/disorder or a neuro-ophthalmologic disorder in a human patient in need thereof comprising, consisting essentially of, or consisting of administering to the human patient a therapeutically effective amount of ibudilast, or a pharmaceutically acceptable salt thereof.

In some embodiments, provided herein are methods of treating ophthalmic disease/disorder or injury associated with a progressive multiple sclerosis in a human patient in need thereof comprising, consisting essentially of, or consisting of administering to the human patient a therapeutically effective amount of ibudilast, or a pharmaceutically acceptable salt thereof.

In some embodiments, provided herein are methods of treating retinal injury associated with a progressive multiple sclerosis in a human patient in need thereof comprising, consisting essentially of, or consisting of administering to the human patient a therapeutically effective amount of ibudilast, or a pharmaceutically acceptable salt thereof.

In some embodiments, provided herein are methods of treating macular injury associated with a progressive multiple sclerosis in a human patient in need thereof comprising, consisting essentially of, or consisting of administering to the human patient a therapeutically effective amount of ibudilast, or a pharmaceutically acceptable salt thereof.

In some embodiments, provided herein are methods of decreasing macular volume loss associated with a progressive multiple sclerosis in a human patient in need thereof comprising, consisting essentially of, or consisting of administering to the human patient a therapeutically effective amount of ibudilast, or a pharmaceutically acceptable salt thereof. In some embodiments, the administration of the ibudilast, or pharmaceutically acceptable salt thereof, decreases macular volume loss in the human patient as compared to no administration of the ibudilast, or pharmaceutically acceptable salt thereof.

The practice of the present disclosure will employ, unless otherwise indicated, conventional methods of chemistry, biochemistry, and pharmacology, within the skill of the art. Such techniques are explained fully in the literature. See, e.g.; A. L. Lehninger, Biochemistry (Worth Publishers, Inc., current addition); Morrison and Boyd, Organic Chemistry (Allyn and Bacon, Inc., current addition); J. March, Advanced Organic Chemistry (McGraw Hill, current addition); Remington: The Science and Practice of Pharmacy, A. Gennaro, Ed., 20th Ed.; FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

All publications cited herein, including internet articles, the FDA Orange Book (available on the FDA's website), books, handbooks, journal articles, patents and patent applications, whether supra or infra, are hereby incorporated by reference in their entirety.

Definitions

Before describing the present disclosure in detail, it is to be understood that this disclosure is not limited to particular administration modes, patient populations, and the like, as such may vary, as will be apparent from the accompanying description and figures.

It must be noted that, as used in this specification and the intended claims, the singular forms "a," "an," and "the" include plural referents unless the context clearly dictates otherwise. Thus, for example, reference to "a drug" includes a single drug as well as two or more of the same or different drugs, reference to "an optional excipient" refers to a single optional excipient as well as two or more of the same or different optional excipients, and the like.

In describing and claiming the present disclosure, the following terminology will be used in accordance with the definitions described below.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention. When an embodiment is defined by one of these terms (e.g., "comprising") it should be understood that this disclosure also includes alternative embodiments, such as "consisting essentially of" and "consisting of" for said embodiment.

"Optional" or "optionally" means that the subsequently described circumstance may or may not occur, so that the description includes instances where the circumstance occurs and instances where it does not.

"Pharmaceutically acceptable excipient or carrier" refers to an excipient that may optionally be included in the compositions of the disclosure and that causes no significant adverse toxicological effects to the patient.

"Pharmaceutically acceptable salt" includes, but is not limited to, amino acid salts, salts prepared with inorganic acids, such as chloride, sulfate, phosphate, diphosphate, bromide, and nitrate salts, or salts prepared from the corresponding inorganic acid form of any of the preceding, e.g., hydrochloride, etc., or salts prepared with an organic acid, such as malate, maleate, fumarate, tartrate, succinate, ethylsuccinate, citrate, acetate, lactate, methanesulfonate, benzoate, ascorbate, para-toluenesulfonate, palmoate, salicylate and stearate, as well as estolate, gluceptate and lactobionate salts. Similarly, salts containing pharmaceutically acceptable cations include, but are not limited to, sodium, potassium, calcium, aluminum, lithium, and ammonium (including substituted ammonium).

"Active molecule" or "active agent" as described herein includes any agent, drug, compound, composition of matter or mixture which provides some pharmacologic, often beneficial, effect that can be demonstrated in vivo or in vitro. This includes foods, food supplements, nutrients, nutraceuticals, drugs, vaccines, antibodies, vitamins, and other beneficial agents. As used herein, the terms further include any physiologically or pharmacologically active substance that produces a localized or systemic effect in a patient. In specific embodiments, the active molecule or active agent includes ibudilast or a pharmaceutically acceptable salt thereof.

"Substantially" or "essentially" means nearly totally or completely, for instance, 95% or greater of some given quantity. In some embodiments, "substantially" or "essentially" means 95%, 96%, 97%, 98%, 99%, 99.5%, or 99.9%.

The terms "subject," "individual" or "patient" are used interchangeably herein and refer to a vertebrate, preferably a mammal. Mammals include, but are not limited to, mice, rodents, rats, simians, humans, farm animals, dogs, cats, sport animals and pets. In this disclosure, subject, individual, or patient is in reference to a human.

The terms "pharmacologically effective amount" or "therapeutically effective amount" of a composition or agent, as provided herein, refer to a nontoxic but sufficient amount of the composition or agent to provide the desired response, such as a reduction or reversal of progressive multiple sclerosis. The exact amount required will vary from subject to subject, depending on the species, age, and general condition of the subject, the severity of the condition being treated, the particular drug or drugs employed, mode of administration, and the like. An appropriate "effective" amount in any individual case may be determined by one of ordinary skill in the art using routine experimentation, based upon the information provided herein.

The term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term. For example, in some embodiments, it will mean plus or minus 5% of the particular term. Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number, which, in the context in which it is presented, provides the substantial equivalent of the specifically recited number.

As used herein, the term "treatment" or "treating" means any treatment of a disease or condition or associated disorder, in a patient, including inhibiting the disease or condition, that is, arresting or suppressing the development of clinical symptoms. "Treatment" or "treating" also includes arresting the development of or reversing the symptom or symptoms of a disease. For purposes of the various aspects and embodiments of the present disclosure, beneficial or desired clinical results include, but are not limited to, reduction, alleviation, or amelioration of one or more manifestations of or negative effects of progressive multiple sclerosis, improvement in one or more clinical outcomes, diminishment of extent of sclerosis, delay or slowing of sclerosis progression, amelioration, palliation, or stabilization of the sclerosis state, and other beneficial results described herein.

In some aspects, the term treating refers to an improvement in clinical outcomes. The term "clinical outcome" refers to any clinical observation or measurement relating to a patient's reaction to a therapy.

Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

Neurodegenerative Diseases/Disorders

Exemplary neurodegenerative diseases/disorders include, but are not limited to, Alzheimer's disease, Senile dementia of the Alzheimer type, or Pick's disease (lobar atrophy), multiple sclerosis, neurodegenerative diseases that include syndromes combining progressive dementia with other prominent neurologic abnormalities, progressive neurodegenerative disease mainly afflicting adults and including progressive neurodegenerative forms of Huntington's disease, multiple system atrophy combining dementia with ataxia and/or manifestation of Parkinson's disease, progressive supranuclear palsy (Steele-Richardson-Olszewski), diffuse Lewy body disease, or corticodentatinigral degeneration. Additional subjects can be suffering from progressive neurodegenerative disease that mainly afflicts young adults and children and include Hallervorden-Spatz disease and progressive familial myoclonic epilepsy, progressive neurodegenerative disease that includes syndromes of gradually developing abnormalities of posture and movement, or disease that includes paralysis agitans (Parkinson's disease), striatonigral degeneration, progressive supranuclear palsy, torsion dystonia (torsion spasm; dystonia musculorum deformans), spasmodic torticollis and other restricted dyskinesias, Familial tremor, or Gilles de la Tourette syndrome, syndromes of progressive ataxia, cerebellar degenerations or spinocerebellar degenerations, cerebellar cortical degeneration or olivopontocerebellar atrophy (OPCA), spinocerebellar degenerations including spinocerebellar degenerations (Friedreich's ataxia and related disorders). Neurodegenerative diseases/disorders include, but are not limited to, central autonomic nervous system failure (Shy-Drager syndrome), syndromes of muscular weakness and wasting without sensory changes (motor neuron disease), amyotrophic lateral sclerosis (ALS), spinal muscular atrophy, infantile spinal muscular atrophy (Werdnig-Hoffmann), juvenile spinal muscular atrophy (Wohlfart-Kugelberg-Welander), or other forms of familial spinal muscular atrophy, primary lateral sclerosis or hereditary spastic paraplegia, syndromes combining muscular weakness and wasting with sensory changes (progressive neural muscular atrophy; chronic familial polyneuropathies), peroneal muscular atrophy (Charcot-Marie-Tooth), hypertrophic interstitial polyneuropathy (Deferine-Sottas), or miscellaneous forms of chronic progressive neuropathy, progressive neurodegenerative diseases that include syndromes of progressive visual loss. Neurodegenerative diseases/disorders include, but are not limited to, pigmentary degeneration of the retina (retinitis pigmentosa), or hereditary optic atrophy (Leber's disease), motor neuron disease and the progressive ataxias; glaucoma; sporadic progressive neurodegenerative diseases, multifocal motor neuropathy with conduction block, motor neuropathy with paraproeinemia, motor-predominant peripheral neuropathies, olivopontocerebellar atrophy, Azorean (Machado-Joseph) disease, familial progressive neurodegenerative diseases such as familial amyotrophic lateral sclerosis, spinal muscular atrophies, familial spastic paraparesis, hereditary biochemical disorders, arthrogryposis multiplex congenital, or progressive juvenile bulbar palsy (Fazio-Londe). Examples of hereditary biochemical disorders are superoxide dismutase deficiency, hexosaminidase A and B deficiency, or androgen receptor mutation (Kennedy's syndrome). Progressive neurodegenerative diseases can include viral and prion diseases, such as HTLV-1 associated myelopathy, progressive multifocal leukoencephalopathy, Creutzfeldt-Jakob disease, Gerstmann-Straussler-Scheinker disease, kuru, fatal familial insomnia, or Alper's disease.

"Progressive neurodegenerative disease" means any neurodegenerative disease that is in the progressive state (that is, getting worse compared to a baseline level) or has such progressive characteristics. Thus, a progressive state is a worsening of symptoms over time and can be precipitous or gradual. Examples of progressive neurodegenerative diseases include Parkinson's disease, amyotrophic lateral sclerosis, Alzheimer's disease, and progressive forms of multiple sclerosis exclusive of relapse/remitting multiple sclerosis.

Neuro-Ophthalmologic Disorders

Exemplary neuro-ophthalmologic disorders include, but are not limited to, papilledema and idiopathic intracranial hypertension (IIH); anterior ischemic optic neuropathy (AION); optic neuritis; ocular motor cranial neuropathy; and Horner syndrome.

Progressive Multiple Sclerosis

Multiple sclerosis (MS) is a complex autoimmune disease with predominantly unknown etiology currently affects approximately 2.5 million people worldwide. Several pathological processes such as inflammation, demyelination, axonal damage and repair mechanisms contribute in the complex disease manifestation of MS. MS is usually a sporadic disease and is characterized as a variably progressive disease of the nervous system in which the patchy degenerative and inflammatory changes occur within the brain and spinal cord. The degenerative and inflammatory changes are associated with the formation of sclerotic plaques due, in part, to abnormal hardening and fibrosis of the neuronal myelin sheath. The symptoms are diverse, ranging from tremor, nystagmus, paralysis, and disturbances in speech and vision. Symptoms of the disease often occur in early adult life with characteristic exacerbations and remissions.

Relapsing remitting multiple sclerosis (RRMS) is the most common type of the disease, accounting for 65%-85% of patients. Most patients with RRMS eventually progress to the secondary progressive (SPMS) form of the disease. Despite recent improvements in pharmacotherapy for relapsing remitting multiple sclerosis (RRMS), there are no therapies generally considered efficacious in progressive MS in the absence of relapses. The few studies showing efficacy of anti-inflammatory therapies in progressive forms of MS were likely driven by the anti-inflammatory effect of the therapies. Currently, mitoxantrone is the only FDA-approved therapy for secondary progressive MS but is not commonly used because of its risks of heart injury and blood cancers (e.g., leukemia). There is a great need for a safe, effective, and conveniently-administered therapy for patients with progressive MS without overt inflammation.

There are four recognized types of multiple sclerosis: (1) Relapsing/Remitting Multiple Sclerosis (RR multiple sclerosis), (2) Secondary Progressive Multiple Sclerosis (SP multiple sclerosis), (3) Progressive Relapsing Multiple Sclerosis (PR multiple sclerosis), and (4) Primary Progressive Multiple Sclerosis (PP multiple sclerosis). RR multiple sclerosis is not considered to fall within the scope of the claims, but the other forms of multiple sclerosis, i.e., SP multiple sclerosis, PR multiple sclerosis and PP multiple sclerosis are considered to be one aspect of the present invention. In all types of progressive MS, there is a loss of function over time regardless of relapses.

"Relapsing/Remitting Multiple Sclerosis (RR multiple Sclerosis) is characterized by relapses (also known as exacerbations) during which time new symptoms can appear and old ones resurface or worsen. The relapses are followed by periods of remission, during which time the person fully or partially recovers from the deficits acquired during the relapse. Relapses can last for days, weeks or months and recovery can be slow and gradual or almost instantaneous. The vast majority of people presenting with Multiple Sclerosis are first diagnosed with relapsing/remitting. This is typically when they are in their twenties or thirties, though diagnoses much earlier or later are known. Around twice as many women as men present with this variety.

In "Secondary Progressive Multiple Sclerosis (SP multiple Sclerosis), a person who initially had relapsing-remitting multiple Sclerosis begins to develop a gradual deterioration in nerve function, with or without relapses. After a number of years many people who have had relapsing/remitting multiple Sclerosis will pass into a secondary progressive phase of the disease. This is characterized by a gradual worsening of the disease between relapses. In the early phases of Secondary Progressive MS, the person may still experience a few relapses but after a while these merge into a general progression. People often do not return to their prior level of function after a relapse. People with Secondary Progressive MS may experience good and bad days or weeks, but, apart from some remission following relapsing episodes, have no real recovery. After 10 years, 50% of people with relapsing/remitting multiple sclerosis will have developed secondary progressive. By 25 to 30 years, that FIGURE will have risen to 90%.

Progressive Relapsing Multiple Sclerosis (PR multiple sclerosis) shows clear progression in the level of disability from the time symptoms first begin, but with episodes of clear relapses that may or may not be associated with some recovery following the acute episode. This form of multiple sclerosis follows a progressive course from onset, punctuated by relapses. There is significant recovery immediately following a relapse but between relapses there is a gradual worsening of symptoms.

Primary Progressive Multiple Sclerosis (PP multiple sclerosis) is characterized by a gradual progression of the disease from its onset with no remissions or relapses at all. There may be periods of a leveling off of disease activity and, as with secondary progressive, there may be good and bad days or weeks. PP multiple sclerosis differs from Relapsing/Remitting MS and Secondary Progressive MS in that onset is typically in the late thirties or early forties, men are as likely women to develop it and initial disease activity is in the spinal cord and not in the brain. Primary Progressive multiple sclerosis often migrates into the brain but is less likely to damage brain areas than relapsing/remitting or secondary progressive—for example, people with Primary Progressive MS are less likely to develop cognitive problems.

In some embodiments, the progressive multiple sclerosis has progressed beyond relapse remitting multiple sclerosis. In some embodiments, the progressive multiple sclerosis is primary progressive multiple sclerosis. In some embodiments, the primary progressive multiple sclerosis is characterized by disease progression from onset, with occasional plateaus and temporary minor improvements allowed, but not distinct relapses. In some embodiments, the progressive multiple sclerosis is secondary progressive multiple sclerosis. In some embodiments, the secondary progressive multiple sclerosis is characterized as an initial relapsing-remitting course, followed by progression, with or without occasional relapses, minor remissions and plateaus.

Ophthalmic Disease/Disorder or Injury Associated with Neurodegenerative Disease/Disorder or a Neuro-Ophthalmologic Disorder In some embodiments, the ophthalmic disease/disorder or injury associated with a neurodegenerative disease/disorder or a neuro-ophthalmologic disorder is retinal injury. In some embodiments, the retinal injury does not occur due to accidental causes. In some embodiments, the retinal injury occurs due to disease or disorder. In some embodiments, retinal injury is macular injury.

In some embodiments, the ophthalmic disease/disorder or injury associated with a neurodegenerative disease/disorder or a neuro-ophthalmologic disorder is macular injury. In some embodiments, the macular injury does not occur due to accidental causes. In some embodiments, the macular injury occurs due to disease or disorder. In some embodiments, macular injury is assessed by measurement of macular volume loss and/or thinning of the granular cell/inner plexiform layer (GCIP).

In some embodiments, the ophthalmic disease/disorder or injury associated with a neurodegenerative disease/disorder or a neuro-ophthalmologic disorder is unilateral internuclear ophthalmoplegia, gaze-evoked nystagmus, saccadic hypermetria, lack of vestibulo-ocular reflex inhibition, or pendular nystagmus.

In some embodiments, the ophthalmic disease/disorder or injury associated with a neurodegenerative disease/disorder or a neuro-ophthalmologic disorder is macular degeneration, retinal degeneration, or diabetic retinopathy. In some embodiments, the ophthalmic disease/disorder or injury associated with a neurodegenerative disease/disorder or a neuro-ophthalmologic disorder is macular degeneration. In some embodiments, the ophthalmic disease/disorder or injury associated with a neurodegenerative disease/disorder or a neuro-ophthalmologic disorder is retinal degeneration. In some embodiments, the ophthalmic disease/disorder or injury associated with a neurodegenerative disease/disorder or a neuro-ophthalmologic disorder is diabetic retinopathy.

Ibudilast

The methods of the disclosure are based upon administration of the molecule, ibudilast. Ibudilast is a small molecule drug (molecular weight of 230.3) having the structure shown below.

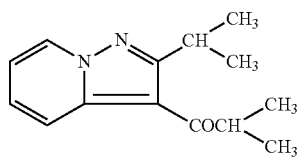

Ibudilast is also found under ChemBank ID 3227, CAS #50847-11-5, and Beilstein Handbook Reference No. 5-24-03-00396. Its molecular formula corresponds to C14H18N2O. Ibudilast is also known by various chemical names including 2-methyl-1-(2-(1-methylethyl)pyrazolo(1,5-a)pyridin-3-yl)1-propanone; 3-isobutyryl-2-isopropylpyrazolo(1,5-a)pyridine; and 1-(2-isopropyl-pyrazolo[1,5-a]pyridin-3-yl)-2-methyl-propan-1-one. Other synonyms for ibudilast include Ibudilastum (Latin), BRN 0656579, KC-404, and MN-166. Its brand name is Ketas®. Ibudilast, as referred to herein, is meant to include any and all pharmaceutically acceptable salt forms thereof, prodrug forms (e.g., the corresponding ketal), solvates, and the like, as appropriate for use in its intended formulation for administration.

Ibudilast is an inhibitor of the macrophage inhibitory factor (MIF). Ibudilast is also a selective inhibitor of cyclic nucleotide phosphodiesterases (PDEs) 3A, 4, 10A1 and 11A1 (Gibson et al., Eur J Pharmacol 538: 39-42, 2006), and has also been reported to have leukotriene D4 and PAF antagonistic activities. Its profile appears effectively anti-inflammatory and unique in comparison to other PDE inhibitors and anti-inflammatory agents. PDEs catalyze the hydrolysis of the phosphoester bond on the 3'-carbon to yield the corresponding 5'-nucleotide monophosphate. Thus, they regulate the cellular concentrations of cyclic nucleotides. Since extracellular receptors for many hormones and neurotransmitters utilize cyclic nucleotides as second messengers, the PDEs also regulate cellular responses to these extracellular signals. There are at least eight classes of PDEs: $Ca_2+$/calmodulin-dependent PDEs (PDE1); cGMP-stimulated PDEs (PDE2); cGMP-inhibited PDEs (PDE3); cAMP-specific PDEs (PDE4); cGMP-binding PDEs (PDE5); photoreceptor PDEs (PDE6); high affinity, cAMP-specific PDEs (PDE7); and high affinity cGMP-specific PDEs (PDE9). Ibudilast acts to suppress inflammation via action on inflammatory cells (e.g., glial cells) resulting in the suppression of both pro-inflammatory mediator and neuroactive mediator release. Ibudilast may also suppress the production of pro-inflammatory cytokines (IL-1β, TNF-α) and may enhance the production of the anti-inflammatory cytokines (IL-4, IL-10). References related to the foregoing include the following: Obernolte, R., et al. (1993) "The cDNA of a human lymphocyte cyclic-AMP phosphodiesterase (PDE IV) reveals a multigene family" Gene 129: 239-247; Rile, G., et al. (2001) "Potentiation of ibudilast inhibition of platelet aggregation in the presence of endothelial cells" Thromb. Res. 102: 239-246; Souness, J. E., et al. (1994) "Possible role of cyclic AMP phosphodiesterases in the actions of ibudilast on eosinophil thromboxane generation and airways smooth muscle tone" Br. J. Pharmacol. 111: 1081-1088; Suzumura, A., et al. (1999) "Ibudilast suppresses TNF.alpha. production by glial cells functioning mainly as type III phosphodiesterase inhibitor in CNS" Brain Res. 837: 203-212; Takuma, K., et al. (2001) "Ibudilast attenuates astrocyte apoptosis via cyclic GMP signaling pathway in an in vitro reperfusion model" Br. J. Pharmacol. 133: 841-848. Ibudilast exhibits good CNS penetration. (Sanftner et al Xenobiotica 2009 39: 964-977).

As stated previously, a reference to any one or more of the herein-described drugs, in particular ibudilast, is meant to encompass, where applicable, any and all enantiomers, mixtures of enantiomers including racemic mixtures, prodrugs, pharmaceutically acceptable salt forms, hydrates (e.g., monohydrates, dihydrates, etc.), solvates, different physical forms (e.g., crystalline solids, amorphous solids), metabolites, and the like.

Methods of Administration

Ibudilast administration may be accomplished through various modes of delivery. Preferred methods of delivery of ibudilast include systemic and localized delivery. Such routes of administration include but are not limited to, oral, intra-arterial, intrathecal, intraspinal, intramuscular, intraperitoneal, intranasal, and inhalation routes.

More particularly, ibudilast of the present disclosure may be administered for therapy by any suitable route, including without limitation, oral, rectal, nasal, topical (including transdermal, aerosol, buccal and sublingual), vaginal, parenteral (including subcutaneous, intravenous, intramuscular, and intradermal), intrathecal, and pulmonary. In some embodiments, the ibudilast is administered orally. In some embodiments, the ibudilast is administered through an injection. The preferred route will, of course, vary with the condition and age of the recipient, the particular syndrome being treated, and the specific combination of drugs employed.

In some embodiments, the ibudilast, or pharmaceutically acceptable salt thereof, is administered orally.

Dosages

Therapeutic amounts can be empirically determined and will vary with the particular condition being treated, the subject, and the efficacy and toxicity of each of the active agents contained in the composition. The actual dose to be administered will vary depending upon the age, weight, and general condition of the subject as well as the severity of the condition being treated and the judgment of the health care professional.

Therapeutically effective amounts can be determined by those skilled in the art and will be adjusted to the requirements of each particular case. Generally, a therapeutically effective amount of ibudilast, or pharmaceutically acceptable salt thereof, will range from a total daily dosage of about 0.1 mg/day-4,000 mg/day, about 0.1 mg/day to 720 mg/day, about 60-600 mg/day, or about 100-480 mg/day, or more preferably, in an amount between about 1-240 mg/day, about 30-240 mg/day, about 30-200 mg/day, about 30-120 mg/day, about 1-120 mg/day, about 50-150 mg/day, about 60-150 mg/day, about 60-120 mg/day, or about 60-100 mg/day, administered as either a single dosage or as multiple dosages. In some embodiments, the therapeutically effective amount of ibudilast, or pharmaceutically acceptable salt thereof, is from about 30-200 mg/day, administered as either a single dosage or as multiple dosages. In some embodiments, multiple dosages include two, three, or four doses per day. In some embodiments, multiple dosages include two or three doses per day.

In some embodiments, the dosage amounts of ibudilast, or pharmaceutically acceptable salt thereof, include dosages greater than about 20 mg BID or TID. In some embodiments, the dosage amount of ibudilast, or pharmaceutically acceptable salt thereof, is greater than about 30 mg/day, 60 mg/day, 80 mg/day, 90 mg/day, 120 mg/day, 150 mg/day, 180 mg/day, 210 mg/day, 240 mg/day, 270 mg/day, 300 mg/day, 360 mg/day, 400 mg/day, 440 mg/day, 480 mg/day, 520 mg/day, 580 mg/day, 600 mg/day, 620 mg/day, 640 mg/day, 680 mg/day, and 720 mg/day or more.

In some embodiments, the therapeutically effective amount of ibudilast, or pharmaceutically acceptable salt thereof, is at least 30 mg/day, at least 40 mg/day, at least 50 mg/day, at least 60 mg/day, at least 70 mg/day, at least 80 mg/day, at least 90 mg/day, at least 100 mg/day, at least 110 mg/day, at least 120 mg/day, at least 130 mg/day, at least 140 mg/day, at least 150 mg/day, at least 160 mg/day, at least 170 mg/day, at least 180 mg/day, at least 190 mg/day, at least 200 mg/day, at least 225 mg/day, at least 250 mg/day, at least 275 mg/day, at least 300 mg/day, at least 325 mg/day, at least 350 mg/day, at least 375 mg/day, at least 400 mg/day, at least 425 mg/day, at least 450 mg/day, at least 475 mg/day, at least 500 mg/day, at least 525 mg/day, at least 550 mg/day, at least 575 mg/day, at least 600 mg/day, at least 625 mg/day, at least 650 mg/day, at least 675 mg/day, at least 700 mg/day, or at least 720 mg/day. In some embodiments, the therapeutically effective amount of ibudilast, or pharmaceutically acceptable salt thereof, is at least 60 mg/day. In some embodiments, the therapeutically effective amount of ibudilast, or pharmaceutically acceptable salt thereof, is at least 30 mg/day. In some embodiments, the therapeutically effective amount of ibudilast, or pharmaceutically acceptable salt thereof, is at least 60 mg/day. In some embodiments, the therapeutically effective amount of ibudilast, or pharmaceutically acceptable salt thereof, is at least 80 mg/day. In some embodiments, the therapeutically effective amount of ibudilast, or pharmaceutically acceptable salt thereof, is at least 100 mg/day.

In some embodiments, the therapeutically effective amount of ibudilast, or pharmaceutically acceptable salt thereof, is about 30 mg/day, about 40 mg/day, about 50 mg/day, about 60 mg/day, about 70 mg/day, about 80 mg/day, about 90 mg/day, about 100 mg/day, about 110 mg/day, about 120 mg/day, about 130 mg/day, about 140 mg/day, about 150 mg/day, about 160 mg/day, about 170 mg/day, about 180 mg/day, about 190 mg/day, about 200 mg/day, about 225 mg/day, about 250 mg/day, about 275 mg/day, about 300 mg/day, about 325 mg/day, about 350 mg/day, about 375 mg/day, about 400 mg/day, about 425 mg/day, about 450 mg/day, about 475 mg/day, about 500 mg/day, about 525 mg/day, about 550 mg/day, about 575 mg/day, about 600 mg/day, about 625 mg/day, about 650 mg/day, about 675 mg/day, about 700 mg/day, or about 720 mg/day. In some embodiments, the therapeutically effective amount of ibudilast, or pharmaceutically acceptable salt thereof, is about 30 mg/day. In some embodiments, the therapeutically effective amount of ibudilast, or pharmaceutically acceptable salt thereof, is about 60 mg/day. In some embodiments, the therapeutically effective amount of ibudilast, or pharmaceutically acceptable salt thereof, is about 60 mg/day. In some embodiments, the therapeutically effective amount of ibudilast, or pharmaceutically acceptable salt thereof, is about 80 mg/day. In some embodiments, the therapeutically effective amount of ibudilast, or pharmaceutically acceptable salt thereof, is about 100 mg/day.

Depending upon the dosage amount and precise condition to be treated, administration can be one, two, three, or four times daily for a time course of one day to several days, weeks, months, and even years, and may even be for the life of the patient. Illustrative dosing regimens will last a period of at least about a week, from about 1-4 weeks, from about 1-8 weeks, from 1-12 weeks, from 1-16 weeks, from 1-20 weeks, from 1-24 weeks, from 1-36 weeks, from 1-48 weeks, from 1-52 weeks, from 1-60 weeks, from 1-72 weeks, from 1-84 weeks, from 1-96 weeks, from 1 week to 1 year, from 1 week to 2 years, from 1 week to 3 years, from 1 week to 4 years, from 1 week to 5 years, or longer. In some embodiments, a dosing regimen is for a period of at least about 12, 24, 36, 48, 60, 72, 84, or 96 weeks. In some embodiments, a dosing regimen is for a period of about 12, 24, 36, 48, 60, 72, 84, or 96 weeks. In some embodiments, a dosing regimen is for a period of at least about 1 year, 2 years, 3 years, 4 years, or 5 years. In some embodiments, a dosing regimen is for a period of about 1 year, 2 years, 3 years, 4 years, or 5 years.

Practically speaking, a unit dose of any given composition of the disclosure or active agent can be administered in a variety of dosing schedules, depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, every other day, three times weekly, twice weekly, once weekly, twice monthly, once monthly, and so forth.

Formulations

The active agents described herein, such as ibudilast, or a pharmaceutically acceptable salt thereof, may be administered in a formulation which may optionally contain one or more additional components as described below.

In one aspect provided herein is a composition comprising, consisting essentially of, or consisting of: (a) a therapeutically effective amount of ibudilast or a pharmaceutically acceptable salt thereof, and (b) at least one pharmaceutically acceptable excipient and/or carrier.

Excipients/Carriers

The compositions of the disclosure may further comprise one or more pharmaceutically acceptable excipients or carriers. Exemplary excipients include, without limitation, polyethylene glycol (PEG), PEG 400, (2-Hydroxypropyl)-β-cyclodextrin, hydrogenated castor oil (HCO), cremophors, carbohydrates, starches (e.g., corn starch), inorganic salts, antimicrobial agents, antioxidants, binders/fillers, surfactants, lubricants (e.g., calcium or magnesium stearate), glidants such as talc, disintegrants, diluents, buffers, acids, bases, film coats, combinations thereof, and the like.

A composition of the disclosure may include one or more carbohydrates such as a sugar, a derivatized sugar such as an alditol, aldonic acid, an esterified sugar, and/or a sugar polymer. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

Also suitable for use in the compositions of the disclosure are potato and corn-based starches such as sodium starch glycolate and directly compressible modified starch.

Further representative excipients include inorganic salt or buffers such as citric acid, sodium chloride, potassium chloride, sodium sulfate, potassium nitrate, sodium phosphate monobasic, sodium phosphate dibasic, and combinations thereof.

A composition of the disclosure may also contain one or more antioxidants. Antioxidants are used to prevent oxidation, thereby preventing the deterioration of the drug(s) or other components of the preparation. Suitable antioxidants for use in the present disclosure include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

Additional exemplary excipients include surfactants such as polysorbates, e.g., "Tween 20" and "Tween 80," and pluronics such as F68 and F88 (both of which are available from BASF, Mount Olive, N.J.), sorbitan esters, lipids (e.g., phospholipids such as lecithin and other phosphatidylcholines, and phosphatidylethanolamines), fatty acids and fatty esters, steroids such as cholesterol, and chelating agents, such as EDTA, zinc and other such suitable cations.

Further, a composition of the disclosure may optionally include one or more acids or bases. Non-limiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Non-limiting examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumarate, and combinations thereof.

The amount of any individual excipient in the composition will vary depending on the role of the excipient, the dosage requirements of the active agent components, and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15% to about 95% by weight of the excipient. In general, the amount of excipient present in an ibudilast composition of the disclosure is selected from the following: at least about 2%, 5%, 10%, 15%, 20%, 25%, 30%, 35%, 40%, 45%, 50%, 55%, 60%, 65%, 70%, 75%, 80%, 85%, 90%, or even 95% by weight.

These foregoing pharmaceutical excipients along with other excipients are described in "Remington: The Science & Practice of Pharmacy", 19th ed., Williams & Williams, (1995), the "Physician's Desk Reference", 52.sup.nd ed., Medical Economics, Montvale, N.J. (1998), and Kibbe, A. H., Handbook of Pharmaceutical Excipients, 3.sup.rd Edition, American Pharmaceutical Association, Washington, D.C., 2000.

Other Actives

A formulation (or kit) in accordance with the disclosure may contain, in addition to ibudilast or a pharmaceutically acceptable salt thereof, and optionally, one or more additional active agents. In some embodiments, the one or more other therapeutic agent is one that possesses a mechanism of action different from that of ibudilast. Such active ingredients can be found listed in the FDA's Orange Book, Goodman & Gilman The Pharmacological Basis of Therapeutics, J. Griffith Hardman, L. L. Limbird, A. Gilman, 11th Ed., 2005, The Merck Manual, 18th edition, 2007, and The Merck Manual of Medical Information 2003.

Sustained Delivery Formulations

In some embodiments, the compositions are formulated in order to improve stability and extend the half-life of ibudilast, or the pharmaceutically acceptable salt thereof. For example, ibudilast, or the pharmaceutically acceptable salt thereof, may be delivered in a controlled or extended-release formulation. Controlled or extended-release formulations are prepared by incorporating ibudilast or the pharmaceutically acceptable salt thereof into a carrier or vehicle such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. Additionally, ibudilast, or the pharmaceutically acceptable salt thereof, can be encapsulated, adsorbed to, or associated with, particulate carriers. Examples of particulate carriers include those derived from polymethyl methacrylate polymers, as well as microparticles derived from poly(lactides) and poly (lactide-co-glycolides), known as PLG. See, e.g., Jeffery et al., Pharm. Res. (1993) 10:362-368; and McGee et al., J. Microencap. (1996).

Extended release polymers suitable for this purpose are known in the art and include hydrophobic polymers such as cellulose ethers. Non-limiting examples of suitable cellulose ethers include ethyl cellulose, cellulose acetate and the like; polyvinyl esters such as polyvinyl acetate, polyacrylic acid esters, methacrylic and acrylate polymers (pH-independent types); high molecular weight polyvinyl alcohols and waxes such as fatty acids and glycerides, methacrylic acid ester neutral polymers, polyvinyl alcohol-maleic anhydride copolymers and the like; ethylacrylate-methylmethacrylate copolymers; aminoalkyl methacrylate copolymers; and mixtures thereof.

Delivery Forms

The compositions described herein encompass all types of formulations, and in particular, those that are suited for systemic or intrathecal administration. Oral dosage forms include tablets, lozenges, capsules, syrups, oral suspensions, emulsions, granules, microbeads, and pellets. In some embodiments, the oral dosage form is a tablet, capsule, granule, or microbead dosage form. In some embodiments, the oral dosage form is a tablet. In some embodiments, the tablet is an extended release tablet. In some embodiments, the oral dosage form is a capsule. In some embodiments, the capsule is an extended release capsule. In some embodiments, the oral dosage form is in a liquid dosage form. In some embodiments, the oral dosage form is an extended release formulation.

Alternative formulations include aerosols, transdermal patches, gels, creams, ointments, suppositories, powders or lyophilates that can be reconstituted, as well as liquids. Examples of suitable diluents for reconstituting solid compositions, e.g., prior to injection, include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned. Preferably, an ibudilast, or pharmaceutically acceptable salt thereof, composition of the disclosure is one suited for oral administration.

In turning now to oral delivery formulations, tablets can be made by compression or molding, optionally with one or more accessory ingredients or additives. Compressed tablets are prepared, for example, by compressing in a suitable tabletting machine, the active ingredients in a free-flowing form such as a powder or granules, optionally mixed with a binder (e.g., povidone, gelatin, hydroxypropylmethyl cellulose), lubricant, inert diluent, preservative, disintegrant (e.g., sodium starch glycolate, cross-linked povidone, cross-linked sodium carboxymethyl cellulose) and/or surface-active or dispersing agent.

Molded tablets are made, for example, by molding in a suitable tabletting machine, a mixture of powdered compounds moistened with an inert liquid diluent. The tablets may optionally be coated or scored and may be formulated so as to provide slow or controlled release of the active ingredients, using, for example, hydroxypropylmethyl cellulose in varying proportions to provide the desired release profile. Tablets may optionally be provided with a coating, such as a thin film, sugar coating, or an enteric coating to provide release in parts of the gut other than the stomach. Processes, equipment, and toll manufacturers for tablet and capsule making are well-known in the art.

Formulations for topical administration in the mouth include lozenges comprising the active ingredients, generally in a flavored base such as sucrose and acacia or tragacanth and pastilles comprising the active ingredients in an inert base such as gelatin and glycerin or sucrose and acacia.

A pharmaceutical composition for topical administration may also be formulated as an ointment, cream, suspension, lotion, powder, solution, paste, gel, spray, aerosol or oil.

Alternatively, the formulation may be in the form of a patch (e.g., a transdermal patch) or a dressing such as a bandage or adhesive plaster impregnated with active ingredients and optionally one or more excipients or diluents. Topical formulations may additionally include a compound that enhances absorption or penetration of the ingredients through the skin or other affected areas, such as dimethylsulfoxidem bisabolol, oleic acid, isopropyl myristate, and D-limonene, to name a few.

For emulsions, the oily phase is constituted from known ingredients in a known manner. While this phase may comprise merely an emulsifier (otherwise known as an emulgent), it desirably comprises a mixture of at least one emulsifier with a fat and/or an oil. Preferably, a hydrophilic emulsifier is included together with a lipophilic emulsifier that acts as a stabilizer. Together, the emulsifier(s) with or without stabilizer(s) make up the so-called emulsifying wax, and the wax together with the oil and/or fat make up the so-called emulsifying ointment base which forms the oily dispersed phase of cream formulations. Illustrative emulgents and emulsion stabilizers include Tween 60, Span 80, cetostearyl alcohol, myristyl alcohol, glyceryl monostearate and sodium lauryl sulfate.

Formulations for rectal administration are typically in the form of a suppository with a suitable base comprising, for example, cocoa butter or a salicylate.

Formulations suitable for vaginal administration generally take the form of a suppository, tampon, cream, gel, paste, foam or spray.

Formulations suitable for nasal administration, wherein the carrier is a solid, include a coarse powder having a particle size, for example, in the range of about 20 to about 500 microns. Such a formulation is typically administered by rapid inhalation through the nasal passage, e.g., from a container of the powder held in proximity to the nose. Alternatively, a formulation for nasal delivery may be in the form of a liquid, e.g., a nasal spray or nasal drops.

Aerosolizable formulations for inhalation may be in dry powder form (e.g., suitable for administration by a dry powder inhaler), or, alternatively, may be in liquid form, e.g., for use in a nebulizer. Nebulizers for delivering an aerosolized solution include the AERx® (Aradigm), the Ultravent® (Mallinkrodt), and the Acorn II® (Marquest Medical Products). A composition of the disclosure may also be delivered using a pressurized, metered dose inhaler (MDI), e.g., the Ventolin® metered dose inhaler, containing a solution or suspension of a combination of drugs as described herein in a pharmaceutically inert liquid propellant, e.g., a chlorofluorocarbon or fluorocarbon.

Formulations suitable for parenteral administration include aqueous and non-aqueous isotonic sterile solutions suitable for injection, as well as aqueous and non-aqueous sterile suspensions.

Parenteral formulations of the disclosure are optionally contained in unit-dose or multi-dose sealed containers, for example, ampoules and vials, and may be stored in a freeze-dried (lyophilized) condition requiring only the addition of the sterile liquid carrier, for example, water for injections, immediately prior to use. Extemporaneous injection solutions and suspensions may be prepared from sterile powders, granules and tablets of the types previously described.

A formulation of the disclosure may also be an extended release formulation, such that each of the drug components is released or absorbed slowly over time, when compared to a non-sustained release formulation. Sustained release formulations may employ pro-drug forms of the active agent, delayed-release drug delivery systems such as liposomes or polymer matrices, hydrogels, or covalent attachment of a polymer such as polyethylene glycol to the active agent.

In addition to the ingredients particularly mentioned above, the formulations of the disclosure may optionally include other agents conventional in the pharmaceutical arts and particular type of formulation being employed, for example, for oral administration forms, the composition for oral administration may also include additional agents as sweeteners, thickeners or flavoring agents.

Kits

Also provided herein is a kit containing at least one composition of the disclosure, accompanied by instructions for use.

For example, in instances in which each of the drugs themselves are administered as individual or separate dosage forms, the kit comprises ibudilast, or pharmaceutically acceptable salt thereof, along with instructions for use. The ibudilast, or pharmaceutically acceptable salt thereof, may be packaged in any manner suitable for administration, so long as the packaging, when considered along with the instructions for administration, clearly indicates the manner in which drug component is to be administered.

For example, in an illustrative kit comprising ibudilast, or pharmaceutically acceptable salt thereof, the kit may be organized by any appropriate time period, such as by day. As an example, for Day 1, a representative kit may comprise unit dosages of each of ibudilast, or pharmaceutically acceptable salt thereof. If the drug is to be administered twice daily, then the kit may contain, corresponding to Day 1, two rows of unit dosage forms of ibudilast, or pharmaceutically acceptable salt thereof, along with instructions for the timing of administration. Various embodiments according to the above may be readily envisioned, and would of course depend upon the corresponding dosage form, recommended dosage, intended patient population, and the like. The packaging may be in any form commonly employed for the packaging of pharmaceuticals, and may utilize any of a number of features such as different colors, wrapping, tamper-resistant packaging, blister packs, dessicants, and the like.

It is to be understood that while the disclosure has been described in conjunction with preferred specific embodiments, the foregoing description as well as the examples that follow are intended to illustrate and not limit the scope of the disclosure. Other aspects, advantages and modifications within the scope of the disclosure will be apparent to those skilled in the art to which the disclosure pertains.

All references mentioned in this application, including any patents, published patent applications, books, handbooks, journal publications, or the FDA Orange Book are hereby incorporated by reference herein, in their entirety.

The following examples are given for the purpose of illustrating various embodiments of the disclosure and are not meant to limit the present disclosure in any fashion. One skilled in the art will appreciate readily that the present disclosure is well adapted to carry out the objects and obtain the ends and advantages mentioned, as well as those objects, ends and advantages inherent herein. The present examples, along with the methods described herein are presently representative of embodiments and are exemplary, and are not intended as limitations on the scope of the disclosure. Changes therein and other uses which are encompassed within the spirit of the disclosure as defined by the scope of the claims will occur to those skilled in the art.

EXAMPLES

Example 1

This was a multicenter, randomized, double-blind, placebo-controlled, parallel-group study designed to evaluate the safety, tolerability and activity of ibudilast administered twice daily over a 96 week period in subjects with primary or secondary progressive multiple sclerosis.

The primary objectives of the study were:
to evaluate the activity of ibudilast (100 mg/d) versus placebo at 96 weeks as measured by quantitative magnetic resonance imaging (MRI) analysis for whole brain atrophy using brain parenchymal fraction (BPF);
to evaluate the safety and tolerability of ibudilast (100 mg/d) versus placebo administered orally in subjects with primary and secondary progressive multiple sclerosis; and to study the effect of ibudilast on macular measures from the SPRINT-MS phase II trial of ibudilast in progressive MS.

The major secondary objectives were to evaluate the activity of ibudilast at 96 weeks versus placebo as measured by:
Diffusion tensor imaging (DTI) in descending pyramidal white matter tracts;
Magnetization transfer ratio (MTR) imaging in normal-appearing brain tissue;
Retinal nerve fiber layer as measured by Optical coherence tomography (OCT); and
Cortical atrophy as measured by cortical longitudinal atrophy detection algorithm (CLADA).

The additional secondary outcomes were to measure the activity of ibudilast at 96 weeks versus placebo on:
Inflammatory disease activity, as measured by T1 lesion volume, T2 lesion volume, and annualized relapse rate;
Disability, as measured by Expanded Disability Status Scale (EDSS) and Multiple Sclerosis Functional Composite (MSFC);
Cognitive impairment as measured by the Symbol Digit Modalities Test and the Selective Reminding Test;
Quality of Life, as measured by Multiple Sclerosis Impact Scale (MSIS-29), EuroQol 5 Dimensions (EQ-5D), and Short Form-36 Health Survey (SF-36); and
Neuropathic pain, as measured by Brief Pain Inventory (BPI).

The first set of tertiary objectives were to evaluate the activity of ibudilast at one year versus placebo as measured by the primary and secondary imaging outcome measures: whole brain atrophy using brain parenchymal fraction (BPF), diffusion tensor imaging (DTI) in descending pyramidal white matter tracts, magnetization transfer ratio (MTR) imaging in normal-appearing brain tissue, retinal nerve fiber layer (RNFL) as measured by Optical coherence tomography (OCT), and cortical atrophy as measured by cortical longitudinal atrophy detection algorithm (CLADA).

The second set of tertiary objectives were to evaluate the activity of ibudilast (MN-166) at 96 weeks versus placebo as measured by, whole-brain gray matter fraction, magnetization transfer ratio (MTR) in gray matter, new T1 lesions since baseline, and new T2 lesions since baseline.

The exploratory objectives include evaluation of the pharmacokinetics (PK) of ibudilast using a population PK approach, correlations of cerebrospinal fluid (CSF) and serum biomarkers with imaging and clinical measures of progressive disability, identification of unique phase 2 endpoints, and composite MRI scales (combining BPF, MTR, and DTI).

Blood samples for analysis of ibudilast and its metabolite, 6,7-dihydrodiol (DHD) were collected during scheduled visits on Weeks 8, 48, and 96. The exact sampling time and time relative to the previous dose was documented in the case report forms. Population P K modeling using the NONMEM program (Icon Development Solution) was used to characterize the pharmacokinetic properties of ibudilast in healthy subjects and subjects with MS. The population analysis evaluated selected covariates to determine if they contributed to differences in PK parameter estimates among individuals. The covariates included demographic variables (age, gender, body weight, and race), creatinine clearance (as a marker of renal function), liver enzyme levels (as a marker of hepatic function), blood chemistry variables, and relevant disease covariates at baseline, among others. Further, the effect of concomitant medications on the pharmacokinetics of ibudilast was also be assessed.

A total of 255 male and female subjects from 21 to 65 years old, inclusive, were enrolled into one of two treatment arms (ibudilast 100 mg/d or matching-placebo). Study population for SPRINT-MS was a mix of primary (53%) and secondary progressive (47%) MS, average age 56 years and median expanded disability status scale (EDSS)=6.0 at baseline. Randomization of subjects was stratified by disease status (PPMS or SPMS), and by immunomodulating therapy status: "untreated", glatiramer acetate (GA), or interferon-beta. Subjects were allowed to continue using of interferon-beta (IFN-β) or glatiramer acetate while participating in this study. During the study, subjects were allowed to change medications from one injectable to the other. Pegylated interferon beta-1 were also allowed (if approved by the FDA). Inhaled and topical steroids are allowed. If a relapse episode occurred, a single course of systemic corticosteroids was permitted, as prescribed by the treating neurologist. Subjects returned to the clinic for follow-up visits on a regular basis at Week 4, 8, 12, 24, 36, 48, 60, 72, 84 and 96.

The following medications were prohibited prior to and during study participation:
Systemic corticosteroid treatment within 3 months prior to screening (inhaled or topical steroids are allowed);
A single course of systemic corticosteroid treatment was allowed for treatment of a clinical relapse
Current use of intermittent systemic corticosteroids (i.e., monthly or bimonthly intravenous methylprednisolone);
Oral immunosuppressants (e.g., azathioprine, methotrexate, cyclosporine, teriflunomide [Aubagio®]) within 6 months of screening;
Mitoxantrone or natalizumab within 6 months of screening;
Fingolimod or dimethyl fumarate [Tecfidera®] within 3 months of screening;
Rituximab or other B-cell therapy within 12 months of screening;
Current use of other MS disease-modifying therapies (DMTs) besides glatiramer acetate and interferon-beta (any formulation).

The following medications are prohibited during study participation: cimetidine, cyclosporine, dronedarone, lopinavir, probenecid, quinidine (including Neudexta), ranolazine, rifampin, ritonavir, and tipranavir.

To participate in the study, the subjects must have had a confirmed diagnosis of secondary progressive MS (SPMS) or primary progressive MS (PPMS) according to 2010 International Panel Criteria, typical MS lesions on brain MRI according to Swanton's MRI Criteria, and clinical evidence of disability progression in the preceding 2 years, as measured by any of the following:
worsening overall EDSS of at least 0.5 points (may be assessed retrospectively, but cannot be during a clinical relapse) or
20% worsening in 25-foot walk (25-FW) or
20% worsening in 9-hole peg test (9-HPT) in either hand.

The double-blind Treatment Phase consisted of a Baseline visit followed by 10 scheduled clinic visits. The Baseline Visit had to have occurred within 45 days following the Screening Visit. At the Baseline Visit (Day 1), subjects who completed all of the screening assessments and continued to meet eligibility criteria were randomized to one of two treatment groups (ibudilast 100 mg/d or placebo) in a 1:1 ratio.

The FIGURE shows the study design. Subjects took their first dose of study medication (30 mg ibudilast or placebo)

on the evening of the Baseline Visit (Day 1). On the morning of Day 2, all subjects begun a 3 capsule BID dosing regimen through Day 14. Subjects randomized to ibudilast started at 60 mg/d (30 mg BID) on Day 2 and remained on 60 mg/d through Day 14. Beginning on Day 15, all subjects increased dosing to 5 capsules BID regimen; those randomized to the ibudilast treatment arm were taking 100 mg/d.

After Day 15, subjects with intolerable side-effects (e.g., nausea, diarrhea, vertigo) were allowed to reduced their dose to either 4 capsules twice a day (80 mg/d for those taking ibudilast) or 3 capsules twice a day (60 mg/d for those taking ibudilast). Subjects with intolerable side-effects (e.g., nausea, diarrhea, vertigo) at the end of Day 14 were allowed to continue taking 3 capsules twice a day at the Investigator's discretion. At the Investigator's discretion, the daily dose of ibudilast were potentially adjusted between 3 capsules twice a day, 4 capsules twice a day, and 5 capsules twice a day over the first 8 weeks of treatment. At the Investigator's discretion, the daily dose of ibudilast could have been divided and taken three times per day if needed to improve tolerability. At the end of the first 8 weeks of treatment, the subject must have maintained their then-current daily dose of study medication (6 capsules per day, 8 capsules per day, or 10 capsules per day). The dosing interval was either twice a day or 3 times per day, at the Investigator's discretion. The dosing interval could also be changed to between twice and three times per day over the course of the entire study, at the Investigator's discretion.

Subjects returned to the clinic for follow-up visits on a regular basis at Week 4, 8, 12, 24, 36, 48, 60, 72, 84 and 96. Subjects who experienced symptoms suggestive of a possible relapse returned to the clinic within three days of notifying the Investigator and underwent the appropriate assessments. Subjects who prematurely discontinued the study medication were asked to continue in a followed off study medication on a semi-annual basis until the end of the study (Week 96).

Select data are shown in Fox et al., The New England Journal of Medicine, 2018, 846-855, which is hereby incorporated by reference in its entirety. Table 1 indicates patient population.

Patients underwent optical coherence tomography (OCT) at baseline and every 24 weeks using either Cirrus (n=183) or Spectralis (n=61) spectral domain devices. Macular volume and granular cell/inner plexiform layer (GCIP) thickness (Cirrus only) was performed at a central reading center by two independent certified readers, and the measurements were averaged to give a final result. Imaging end points were assessed for differences in rates of change between the trial groups over time using linear mixed models. Analysis was according to modified intent-to-treat (ITT) and included all available values in the statistical analysis.

Macular measurements at baseline are presented in Table 2. The primary OCT outcome, difference between treatment groups in pRNFL change over time in all patients, showed an estimated reduction of 0.305 µM (95% CI: −0.1786 to 0.7893) per year of pRNFL loss with ibudilast. Estimated rate of pRNFL loss per year was −0.2630 µM (95% CI: −0.5973 to 0.0714) in the placebo group compared to 0.0424 µM (95% CI: −0.3091 to 0.3939) in the ibudilast arm. In patients followed with Spectralis OCT, the estimated rate of macular volume change was −0.00503 mm$^3$ (95% CI: −0.02693 to 0.01688) per year for ibudilast and −0.03659 mm$^3$ (95% CI: −0.05824 to 0.01494) per year for placebo (p=0.044); in patients followed with Cirrus OCT, the estimated rate of macular volume change was −0.00040 mm$^3$ (95% CI: −0.02167 to 0.020866) per year for ibudilast and −0.02083 (95% CI: −0.04134 to −0.00033) for placebo (p=0.1734). Rates of macular volume loss were reduced in the ibudilast group measured by Spectralis OCT (between-group difference 0.0316 mm$^3$ per year, 95% CI: 0.0008 to 0.0623), and by Cirrus OCT (between-group difference 0.0204 mm$^3$ per year, 95% CI: −0.0090 to 0.0499). Ganglion cell-inner plexiform layer thinning also showed a directional change in favor of ibudilast (between-group difference 0.4695 µM per year, 95% CI: −0.1189 to 1.0578).

Annual macular volume loss using Spectralis OCT over 96 weeks was slower with ibudilast compared to placebo. Cirrus OCT demonstrated favorable changes towards reduced macular volume loss and GCIP layer thinning.

TABLE 1

| Patient population | | |
|---|---|---|
|  | ibudilast (N = 129) | placebo (N = 126) |
| primary progressive MS | 68 | 66 |
| secondary progressive MS with relapse | 9 | 6 |
| secondary progressive MS without relapse | 52 | 54 |

TABLE 2

| Macular measurements at baseline | | |
|---|---|---|
|  | Ibudilast mean (SD) N | Placebo mean (SD) N |
| Baseline MV Spectralis | 8.26 mm$^3$ (0.46) N = 30 | 8.12 mm$^3$ (0.46) N = 30 |
| Baseline MV Cirrus | 9.70 mm$^3$ (0.54) N = 90 | 9.59 mm$^3$ (0.58) N = 91 |
| Baseline GCIP Cirrus | 71.69 µM (8.98) N = 90 | 68.89 µM (9.71) N = 90 |

EQUIVALENTS

It should be understood that although the present disclosure has been specifically disclosed by certain embodiments and optional features, modification, improvement and variation of the disclosures embodied disclosed herein may be resorted to by those skilled in the art, and that such modifications, improvements and variations are considered to be within the scope of this disclosure. The materials, methods, and examples provided here are representative of certain embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

The use of the term "or" in the claims is used to mean "and/or" unless explicitly indicated to refer to alternatives only or the alternatives are mutually exclusive, although the disclosure supports a definition that refers to only alternatives and "and/or."

Para. A. A method of treating ophthalmic disease/disorder or injury associated with a neurodegenerative disease/disorder or a neuro-ophthalmologic disorder in a human patient in need thereof comprising administering to the human patient a therapeutically effective amount of ibudilast, or a pharmaceutically acceptable salt thereof.

Para. B. The method of Para. A, wherein the ophthalmic disease/disorder or injury is macular injury.

Para. C. The method of Para. A or Para. B, wherein the neurodegenerative disease/disorder is progressive multiple sclerosis.

Para. D. A method of decreasing macular volume loss associated with a progressive multiple sclerosis in a human patient in need thereof comprising administering to the human patient a therapeutically effective amount of ibudilast, or a pharmaceutically acceptable salt thereof.

Para. E. The method of Para. D, wherein the administration of the ibudilast, or pharmaceutically acceptable salt thereof, decreases macular volume loss in the human patient as compared to no administration of the ibudilast, or pharmaceutically acceptable salt thereof.

Para. F. The method of any one of Paras. C-E, wherein the progressive multiple sclerosis has progressed beyond relapse remitting multiple sclerosis.

Para. G. The method of any one of Paras. C-E, wherein the progressive multiple sclerosis is primary progressive multiple sclerosis.

Para. H. The method of Para. G, wherein the primary progressive multiple sclerosis is characterized by disease progression from onset, with occasional plateaus and temporary minor improvements allowed, but not distinct relapses.

Para. I. The method of any one of Paras. C-E, wherein the progressive multiple sclerosis is secondary progressive multiple sclerosis.

Para. J. The method of Para. I, wherein the secondary progressive multiple sclerosis is characterized as an initial relapsing-remitting course, followed by progression, with or without occasional relapses, minor remissions and plateaus.

Para. K. The method of any one of Paras. A-J wherein the ibudilast, or pharmaceutically acceptable salt thereof, is administered for at least about 12, 24, 36, 48, 60, 72, 84, or 96 weeks.

Para. L. The method of any one of Paras. A-J, wherein the ibudilast, or pharmaceutically acceptable salt thereof, is administered for at least about 1 year, 2 years, 3 years, 4 years, or 5 years.

Para. M. The method of any one of Paras. A-J, wherein the ibudilast, or pharmaceutically acceptable salt thereof, is administered for 1 year, 2 years, 3 years, 4 years, or 5 years.

Para. N. The method of any one of Paras. A-M, wherein the ibudilast, or pharmaceutically acceptable salt thereof, is administered orally.

Para. O. The method of Para. N, wherein the ibudilast, or pharmaceutically acceptable salt thereof, is administered in a tablet, capsule, granule, or microbead dosage form.

Para. P. The method of Para. N, wherein the ibudilast, or pharmaceutically acceptable salt thereof, is administered in in a liquid dosage form.

Para. Q. The method of any one of Paras. A-P, wherein the ibudilast, or pharmaceutically acceptable salt thereof, is formulated as an extended release formulation.

Para. R. The method of any one of Paras. A-Q, wherein the ibudilast, or pharmaceutically acceptable salt thereof, is administered in an amount of from about 0.1 mg/day to about 4,000 mg/day.

Para. S. The method of any one of Paras. A-R, wherein the ibudilast, or pharmaceutically acceptable salt thereof, is administered in an amount of from about 0.1 mg/day to about 720 mg/day.

Para. T. The method of any one of Paras. A-Q, wherein the ibudilast, or pharmaceutically acceptable salt thereof, is administered in an amount of at least about 30 mg/day.

Para. U. The method of any one of Paras. A-Q, wherein the ibudilast, or pharmaceutically acceptable salt thereof, is administered in an amount of from about 30 mg/day to about 200 mg/day.

Para. V. The method of any one of Paras. A-Q, wherein the ibudilast, or pharmaceutically acceptable salt thereof, is administered in an amount of from about 60 mg/day to about 600 mg/day.

Para. W. The method of any one of Paras. A-Q, wherein the ibudilast, or pharmaceutically acceptable salt thereof, is administered in an amount of from about 60 mg/day to about 100 mg/day.

Para. X. The method of any one of claims Paras. A-Q, wherein the ibudilast, or pharmaceutically acceptable salt thereof, is administered in an amount of from about 100 mg/day to about 480 mg/day.

Para. Y. The method of any one of claims Paras. A-Q, wherein the ibudilast, or pharmaceutically acceptable salt thereof, is administered in an amount of about 30 mg/day, about 60 mg/day, about 80 mg/day, about 90 mg/day, about 100 mg/day, about 120 mg/day, about 150 mg/day, about 180 mg/day, about 210 mg/day, about 240 mg/day, about 270 mg/day, about 300 mg/day, about 360 mg/day, about 400 mg/day, about 440 mg/day, about 480 mg/day, about 520 mg/day, about 580 mg/day, about 600 mg/day, about 620 mg/day, about 640 mg/day, about 680 mg/day, or about 720 mg/day.

Para. Z. The method of Para. Y, wherein the ibudilast, or pharmaceutically acceptable salt thereof, is administered in an amount of about 60 mg/day, about 80 mg/day, or about 100 mg/day.

Para. AA. The method of any one of Paras. R-Z, wherein the amount of ibudilast, or pharmaceutically acceptable salt thereof, administered per day is divided into one, two or three portions.

What is claimed is:

1. A method of treating ophthalmic disease/disorder or injury associated with a neurodegenerative disease/disorder or a neuro-ophthalmologic disorder in a human patient in need thereof comprising administering to the human patient a therapeutically effective amount of ibudilast, or a pharmaceutically acceptable salt thereof.

2. The method of claim 1, wherein the ophthalmic disease/disorder or injury is macular injury.

3. The method of claim 1, wherein the neurodegenerative disease/disorder is progressive multiple sclerosis.

4. The method of claim 3, wherein administration results in a decrease of macular volume loss associated with a progressive multiple sclerosis in a human patient.

5. The method of claim 4, wherein the administration of the ibudilast, or pharmaceutically acceptable salt thereof, decreases macular volume loss in the human patient as compared to no administration of the ibudilast, or pharmaceutically acceptable salt thereof.

6. The method of claim 3, wherein the progressive multiple sclerosis has progressed beyond relapse remitting multiple sclerosis.

7. The method of claim 3, wherein the progressive multiple sclerosis is primary progressive multiple sclerosis.

8. The method of claim 7, wherein the primary progressive multiple sclerosis is characterized by disease progression from onset, with occasional plateaus and temporary minor improvements allowed, but not distinct relapses.

9. The method of claim 3 wherein the progressive multiple sclerosis is secondary progressive multiple sclerosis.

10. The method of claim 9, wherein the secondary progressive multiple sclerosis is characterized as an initial relapsing-remitting course, followed by progression, with or without occasional relapses, minor remissions and plateaus.

11. The method of claim 1, wherein the ibudilast, or pharmaceutically acceptable salt thereof, is administered for at least about 12, 24, 36, 48, 60, 72, 84, or 96 weeks.

12. The method of claim 1, wherein the ibudilast, or pharmaceutically acceptable salt thereof, is administered for at least about 1 year, 2 years, 3 years, 4 years, or 5 years.

13. The method of claim 1, wherein the ibudilast, or pharmaceutically acceptable salt thereof, is administered orally.

14. The method of claim 1, wherein the ibudilast, or pharmaceutically acceptable salt thereof, is administered in a tablet, capsule, granule, or microbead dosage form.

15. The method of claim 1, wherein the ibudilast, or pharmaceutically acceptable salt thereof, is administered in in a liquid dosage form.

16. The method of claim 1, wherein the ibudilast, or pharmaceutically acceptable salt thereof, is formulated as an extended release formulation.

17. The method of claim 1, wherein the ibudilast, or pharmaceutically acceptable salt thereof, is administered in an amount of from about 0.1 mg/day to about 4,000 mg/day.

18. The method of claim 1, wherein the ibudilast, or pharmaceutically acceptable salt thereof, is administered in an amount of from about 60 mg/day to about 600 mg/day.

19. The method of claim 1, wherein the ibudilast, or pharmaceutically acceptable salt thereof, is administered in an amount of about 30 mg/day, about 60 mg/day, about 80 mg/day, about 90 mg/day, about 100 mg/day, about 120 mg/day, about 150 mg/day, about 180 mg/day, about 210 mg/day, about 240 mg/day, about 270 mg/day, about 300 mg/day, about 360 mg/day, about 400 mg/day, about 440 mg/day, about 480 mg/day, about 520 mg/day, about 580 mg/day, about 600 mg/day, about 620 mg/day, about 640 mg/day, about 680 mg/day, or about 720 mg/day.

20. The method of claim 18, wherein the amount of ibudilast, or pharmaceutically acceptable salt thereof, administered per day is divided into one, two or three portions.

* * * * *